(12) United States Patent
Thapliyal et al.

(10) Patent No.: US 10,850,133 B2
(45) Date of Patent: Dec. 1, 2020

(54) SYSTEM AND METHOD FOR ANATOMICAL MAPPING OF TISSUE AND PLANNING ABLATION PATHS THEREIN

(71) Applicant: Auris Health, Inc., Redwood City, CA (US)

(72) Inventors: Hira V. Thapliyal, Los Altos, CA (US); David A. Gallup, Alameda, CA (US); James W. Arenson, Woodside, CA (US)

(73) Assignee: Auris Health, Inc., Redwood City, CA (US)

(*) Notice: Subject to any disclaimer, the term of this patent is extended or adjusted under 35 U.S.C. 154(b) by 392 days.

(21) Appl. No.: 15/695,562

(22) Filed: Sep. 5, 2017

(65) Prior Publication Data

US 2018/0126193 A1 May 10, 2018

Related U.S. Application Data

(63) Continuation of application No. 14/922,010, filed on Oct. 23, 2015, now abandoned, which is a
(Continued)

(51) Int. Cl.
*A61N 7/02* (2006.01)
*G06F 19/00* (2018.01)
(Continued)

(52) U.S. Cl.
CPC ........... *A61N 7/022* (2013.01); *G06F 19/321* (2013.01); *G16H 15/00* (2018.01); *G16H 20/40* (2018.01);
(Continued)

(58) Field of Classification Search
CPC .............. A61B 18/12; A61B 18/14; A61B 2017/00039; A61B 2090/3782;
(Continued)

(56) References Cited

U.S. PATENT DOCUMENTS 4,641,649 A 2/1987 Walinsky et al.
4,757,820 A 7/1988 Itoh
(Continued)

FOREIGN PATENT DOCUMENTS

DE 10037660 A1 2/2002
WO WO-9902096 A1 1/1999
(Continued)

OTHER PUBLICATIONS

Office Action dated Jan. 17, 2017 for U.S. Appl. No. 14/922,010.
(Continued)

*Primary Examiner* — Michael F Peffley
(74) *Attorney, Agent, or Firm* — Chang & Hale LLP

(57) ABSTRACT

Methods for ablating tissue in a patient having atrial fibrillation comprise advancing an elongate flexible shaft through a patient's vasculature into a chamber of a heart. The elongate flexible shaft has an energy source and a sensor. Tissue in the heart is scanned with the sensor and data about the tissue is captured. The captured data is grouped into one of a plurality of tissue classifications and an anatomical map of the tissue showing the grouped data is displayed. At least a portion of the tissue is ablated so as to form a conduction block that blocks aberrant electrical pathways in the heart. The ablated tissue is grouped into one or more predefined tissue classifications during or prior to the ablation.

15 Claims, 5 Drawing Sheets

Related U.S. Application Data continuation of application No. 12/609,705, filed on Oct. 30, 2009, now Pat. No. 9,192,789.

(60) Provisional application No. 61/109,889, filed on Oct. 30, 2008, provisional application No. 61/109,893, filed on Oct. 30, 2008.

(51) Int. Cl.

| | | |
|---|---|---|
| *G16H 15/00* | (2018.01) | |
| *G16H 20/40* | (2018.01) | |
| *A61B 8/08* | (2006.01) | |
| *A61B 8/12* | (2006.01) | |
| *A61B 8/14* | (2006.01) | |
| *A61B 17/00* | (2006.01) | |
| *A61B 90/00* | (2016.01) | |
| *A61B 34/10* | (2016.01) | |
| *A61N 7/00* | (2006.01) | |

(52) U.S. Cl.
CPC ........... *A61B 8/0883* (2013.01); *A61B 8/0891* (2013.01); *A61B 8/12* (2013.01); *A61B 8/14* (2013.01); *A61B 34/10* (2016.02); *A61B 2017/00039* (2013.01); *A61B 2090/3782* (2016.02); *A61N 2007/0052* (2013.01)

(58) Field of Classification Search
CPC ..... A61B 34/10; A61B 8/0883; A61B 8/0891; A61N 2007/0052; A61N 7/022; G06F 19/321; G16H 15/00; G16H 20/40
See application file for complete search history.

(56) References Cited

U.S. PATENT DOCUMENTS

| | | |
|---|---|---|
| 5,164,920 A | 11/1992 | Bast et al. |
| 5,246,438 A | 9/1993 | Langberg |
| 5,295,484 A | 3/1994 | Marcus et al. |
| 5,314,466 A | 5/1994 | Stern et al. |
| 5,405,346 A | 4/1995 | Grundy et al. |
| 5,433,198 A | 7/1995 | Desai |
| 5,471,988 A | 12/1995 | Fujio et al. |
| 5,568,809 A * | 10/1996 | Ben-haim .............. A61B 5/0464 600/433 |
| 5,718,241 A | 2/1998 | Ben-Haim et al. |
| 5,735,811 A | 4/1998 | Brisken |
| 5,971,983 A | 10/1999 | Lesh |
| 6,012,457 A | 1/2000 | Lesh |
| 6,023,638 A | 2/2000 | Swanson |
| 6,024,740 A | 2/2000 | Lesh et al. |
| 6,052,576 A | 4/2000 | Lambourg |
| 6,064,902 A | 5/2000 | Haissaguerre et al. |
| 6,086,532 A | 7/2000 | Panescu et al. |
| 6,115,626 A | 9/2000 | Whayne et al. |
| 6,117,101 A | 9/2000 | Diederich et al. |
| 6,161,543 A | 12/2000 | Cox et al. |
| 6,164,283 A | 12/2000 | Lesh |
| 6,237,605 B1 | 5/2001 | Vaska et al. |
| 6,245,064 B1 | 6/2001 | Lesh et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,599 B1 | 7/2001 | Lesh et al. |
| 6,261,312 B1 | 7/2001 | Dobak, III et al. |
| 6,277,116 B1 | 8/2001 | Utely et al. |
| 6,305,378 B1 | 10/2001 | Lesh |
| 6,311,090 B1 | 10/2001 | Knowlton |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,379,378 B1 | 4/2002 | Werneth et al. |
| 6,383,151 B1 | 5/2002 | Diederich et al. |
| 6,387,089 B1 | 5/2002 | Kreindel et al. |
| 6,416,511 B1 | 7/2002 | Lesh et al. |
| 6,468,296 B1 | 10/2002 | Dobak, III et al. |
| 6,474,340 B1 | 11/2002 | Vaska et al. |
| 6,475,231 B2 | 11/2002 | Dobak et al. |
| 6,478,811 B1 | 11/2002 | Dobak, III et al. |
| 6,478,812 B2 | 11/2002 | Dobak et al. |
| 6,484,727 B1 | 11/2002 | Vaska et al. |
| 6,491,039 B1 | 12/2002 | Dobak, III |
| 6,491,716 B2 | 12/2002 | Dobak et al. |
| 6,500,121 B1 | 12/2002 | Slayton et al. |
| 6,500,174 B1 | 12/2002 | Maguire et al. |
| 6,502,576 B1 | 1/2003 | Lesh |
| 6,514,244 B2 | 2/2003 | Pope et al. |
| 6,514,249 B1 | 2/2003 | Maguire et al. |
| 6,517,536 B2 | 2/2003 | Hooven et al. |
| 6,529,756 B1 | 3/2003 | Phan et al. |
| 6,533,804 B2 | 3/2003 | Dobak et al. |
| 6,540,771 B2 | 4/2003 | Dobak et al. |
| 6,542,781 B1 | 4/2003 | Koblish et al. |
| 6,546,935 B2 | 4/2003 | Hooven |
| 6,547,788 B1 | 4/2003 | Maguire et al. |
| 6,551,349 B2 | 4/2003 | Lasheras et al. |
| 6,576,001 B2 | 6/2003 | Werneth et al. |
| 6,585,752 B2 | 7/2003 | Dobak et al. |
| 6,592,576 B2 | 7/2003 | Andrews et al. |
| 6,595,989 B1 | 7/2003 | Schaer |
| 6,599,288 B2 | 7/2003 | Maguire et al. |
| 6,602,276 B2 | 8/2003 | Dobak, III et al. |
| 6,605,084 B2 | 8/2003 | Acker et al. |
| 6,607,502 B1 | 8/2003 | Maguire et al. |
| 6,607,527 B1 | 8/2003 | Ruiz et al. |
| 6,613,046 B1 | 9/2003 | Jenkins et al. |
| 6,635,054 B2 | 10/2003 | Fjield et al. |
| 6,645,199 B1 | 11/2003 | Jenkins et al. |
| 6,645,202 B1 | 11/2003 | Pless et al. |
| 6,648,908 B2 | 11/2003 | Dobak et al. |
| 6,652,515 B1 | 11/2003 | Maguire et al. |
| 6,652,517 B1 | 11/2003 | Hall et al. |
| 6,666,614 B2 | 12/2003 | Fechter et al. |
| 6,666,858 B2 | 12/2003 | Lafontaine |
| 6,669,655 B1 | 12/2003 | Acker et al. |
| 6,669,687 B1 | 12/2003 | Saadat |
| 6,676,688 B2 | 1/2004 | Dobak et al. |
| 6,676,689 B2 | 1/2004 | Dobak et al. |
| 6,676,690 B2 | 1/2004 | Werneth |
| 6,685,732 B2 | 2/2004 | Kramer |
| 6,689,128 B2 | 2/2004 | Sliwa et al. |
| 6,692,488 B2 | 2/2004 | Dobak et al. |
| 6,695,873 B2 | 2/2004 | Dobak et al. |
| 6,701,931 B2 | 3/2004 | Sliwa et al. |
| 6,702,842 B2 | 3/2004 | Dobak et al. |
| 6,711,444 B2 | 3/2004 | Koblish |
| 6,719,755 B2 | 4/2004 | Sliwa et al. |
| 6,745,080 B2 | 6/2004 | Koblish |
| 6,752,805 B2 | 6/2004 | Maguire et al. |
| 6,758,847 B2 | 7/2004 | Maguire |
| 6,763,722 B2 | 7/2004 | Fjield et al. |
| 6,773,402 B2 * | 8/2004 | Govari ................. A61B 5/0422 600/459 |
| 6,780,183 B2 | 8/2004 | Jimenez et al. |
| 6,786,218 B2 | 9/2004 | Dobak et al. |
| 6,805,128 B1 | 10/2004 | Pless et al. |
| 6,805,129 B1 | 10/2004 | Pless et al. |
| 6,814,733 B2 | 11/2004 | Scwartz et al. |
| 6,840,936 B2 | 1/2005 | Sliwa et al. |
| 6,858,026 B2 | 2/2005 | Sliwa et al. |
| 6,869,431 B2 | 3/2005 | Maguire et al. |
| 6,872,205 B2 | 3/2005 | Lesh et al. |
| 6,889,694 B2 | 5/2005 | Hooven |
| 6,893,438 B2 | 5/2005 | Hall et al. |
| 6,896,673 B2 | 5/2005 | Hooven |
| 6,899,710 B2 | 5/2005 | Hooven |
| 6,899,711 B2 | 5/2005 | Stewart et al. |
| 6,904,303 B2 | 6/2005 | Phan et al. |
| 6,905,494 B2 | 6/2005 | Yon et al. |
| 6,905,498 B2 | 6/2005 | Hooven |
| 6,905,509 B2 | 6/2005 | Dobak et al. |
| 6,908,464 B2 | 6/2005 | Jenkins et al. |
| 6,920,883 B2 | 7/2005 | Bessette et al. |

(56) References Cited

U.S. PATENT DOCUMENTS

| | | | |
|---|---|---|---|
| 6,923,806 B2 | 8/2005 | Hooven et al. | |
| 6,923,808 B2 | 8/2005 | Taimisto | |
| 6,929,639 B2 | 8/2005 | Lafontaine | |
| 6,932,811 B2 | 8/2005 | Hooven et al. | |
| 6,949,095 B2 | 9/2005 | Vaska et al. | |
| 6,949,097 B2 | 9/2005 | Stewart et al. | |
| 6,953,460 B2 | 10/2005 | Maguire et al. | |
| 6,954,977 B2 | 10/2005 | Maguire et al. | |
| 6,955,173 B2 | 10/2005 | Lesh | |
| 6,964,660 B2 | 11/2005 | Maguire et al. | |
| 6,966,908 B2 | 11/2005 | Maguire et al. | |
| 6,971,394 B2 | 12/2005 | Sliwa et al. | |
| 6,974,454 B2 | 12/2005 | Hooven | |
| 6,984,233 B2 | 1/2006 | Hooven | |
| 6,996,908 B2 | 2/2006 | Orloff et al. | |
| 6,997,925 B2 | 2/2006 | Maguire et al. | |
| 7,001,378 B2 | 2/2006 | Yon et al. | |
| 7,001,383 B2 * | 2/2006 | Keidar | A61B 18/1492 600/509 |
| 7,001,415 B2 | 2/2006 | Hooven | |
| 7,044,135 B2 | 5/2006 | Lesh | |
| 7,063,682 B1 | 6/2006 | Whayne et al. | |
| 7,142,905 B2 | 11/2006 | Slayton et al. | |
| 7,275,450 B2 | 10/2007 | Hirai et al. | |
| 7,285,116 B2 | 10/2007 | Rama et al. | |
| 7,306,593 B2 * | 12/2007 | Keidar | A61B 5/06 606/34 |
| 7,393,325 B2 | 7/2008 | Barthe et al. | |
| 7,633,502 B2 * | 12/2009 | Willis | A61B 5/0422 345/420 |
| 7,681,579 B2 | 3/2010 | Schwartz | |
| 8,403,925 B2 * | 3/2013 | Miller | A61B 18/1233 606/34 |
| 8,454,589 B2 * | 6/2013 | Deno | A61B 18/1492 606/34 |
| 9,155,588 B2 | 10/2015 | Thapliyal et al. | |
| 9,192,789 B2 | 11/2015 | Thapliyal et al. | |
| 2002/0087151 A1 | 7/2002 | Mody et al. | |
| 2003/0050630 A1 | 3/2003 | Mody et al. | |
| 2003/0050631 A1 | 3/2003 | Mody et al. | |
| 2003/0078509 A1 * | 4/2003 | Panescu | A61B 5/06 600/509 |
| 2005/0049582 A1 | 3/2005 | Debenedictis et al. | |
| 2005/0165388 A1 | 7/2005 | Bhola | |
| 2005/0267453 A1 | 12/2005 | Wong et al. | |
| 2006/0122508 A1 | 6/2006 | Slayton et al. | |
| 2007/0027445 A1 | 2/2007 | Gifford et al. | |
| 2007/0265609 A1 | 11/2007 | Thapliyal et al. | |
| 2007/0265610 A1 | 11/2007 | Thapliyal et al. | |
| 2008/0039746 A1 | 2/2008 | Hissong et al. | |
| 2008/0077200 A1 | 3/2008 | Bendett et al. | |
| 2009/0312673 A1 | 12/2009 | Thapliyal et al. | |
| 2009/0312693 A1 | 12/2009 | Thapliyal et al. | |
| 2010/0016762 A1 | 1/2010 | Thapliyal et al. | |
| 2010/0049099 A1 | 2/2010 | Thapliyal et al. | |
| 2010/0114094 A1 | 5/2010 | Thapliyal et al. | |
| 2016/0038772 A1 | 2/2016 | Hira et al. | |

FOREIGN PATENT DOCUMENTS

| | | |
|---|---|---|
| WO | WO-2005117734 A2 | 12/2005 |
| WO | WO-2006034000 A1 | 3/2006 |
| WO | WO-2005117734 A3 | 12/2006 |

OTHER PUBLICATIONS

A new treatment for atrial fibrillation? Feb. 2006, Medical Device & Diagnostic Industry, Medical Device Link, http://www.devicelink.com/mddi/archive/06/02/013.html.

Bushberg, et al.; The essential physics of medical imaging. 2nd Ed.; Lippincott Williams & Wilkins; 2002; 491.

Cox, et al. Current status of the Maze procedure for the treatment of atrial fibrillation. Seminars in Thoracic & Cardiovascular Surgery. 2000; 12:15-19.

Cox, et al. Electrophysiologic basis, surgical development, and clinical results of the maze procedure for atrial flutter and atrial fibrillation. Advances in Cardiac Surgery. 1995; 6:1-67.

Cox, et al. Modification of the maze procedure for atrial flutter and atrial fibrillation. II, Surgical technique of the maze III procedure. Journal of Thoracic & Cardiovascular Surgery. 1995;110:485-95.

Cox, et al. The development of the Maze procedure for the treatment of atrial fibrillation. Seminars in Thoracic & Cardiovascular Surgery. 2000; 12:2-14.

Gentry, et al. Integrated Catheter for 3-D Intracardiac Echocardiography and Ultrasound Ablation. IEEE Transactions on Ultrasonics, Ferroelectrics, and Frequency Control. 2004;51(7):800-808.

Gill. How to perform pulmonary vein isolation. Europace. 2004; 6(2):83-91.

Gillinov, et al. Atrial fibrillation: current surgical options and their assessment. Annals of Thoracic Surgery. 2002;74:2210-7.

Haissaguerre, et al. Spontaneous Initiation of Atrial Fibrillation by Ectopic Beats Originating in the Pulmonary Veins. New England J Med. 1998; 339:659-666.

Levinson. Endocardial Microwave Ablation: A New Surgical Approach for Atrial Fibrillation. The Heart urgery Forum. 2006.

Maessen, et al. Beating heart surgical treatment of atrial fibrillation with microwave ablation. Ann Thorac Surg. 2002; 74: 1160-8.

Nathan, et al. The junction between the left atrium and the pulmonary veins, an anatomic study of human hearts. Circulation. 1966; 34:412-422.

Notice of allowance dated Jul. 21, 2015 for U.S. Appl. No. 12/609,705.
Notice of allowance dated Aug. 7, 2015 for U.S. Appl. No. 12/609,705.
Office action dated Jan. 3, 2013 for U.S. Appl. No. 12/609,705.
Office action dated Feb. 24, 2015 for U.S. Appl. No. 12/609,705.
Office action dated May 30, 2013 for U.S. Appl. No. 12/609,705.
Office action dated Jul. 29, 2014 for U.S. Appl. No. 12/609,705.

Sueda, et al. Efficacy of a simple left atrial procedure for chronic atrial fibrillation in mitral valve operations. Ann Thorac Surg. 1997; 63:1070-1075.

Sueda, et al. Simple left atrial procedure for chronic atrial fibrillation associated with mitral valve disease. Ann Thorac Surg 1996; 62:1796-1800.

Ter Haar. Acoustic surgery. Physics Today. Dec. 2001; 54(12):29-34.

\* cited by examiner

SYSTEM AND METHOD FOR ANATOMICAL MAPPING OF TISSUE AND PLANNING ABLATION PATHS THEREIN

CROSS-REFERENCES TO RELATED APPLICATIONS

The present application is a continuation of U.S. patent application Ser. No. 14/922,010 filed Oct. 23, 2015, now abandoned, which is a continuation of U.S. patent application Ser. No. 12/609,705 filed Oct. 30, 2009, now U.S. Pat. No. 9,192,789 which claims the benefit of US Provisional Patent Application Nos. 61/109,889 filed Oct. 30, 2008, and 61/109,893 filed Oct. 30, 2008; the entire contents of each is incorporated herein by reference The present application is also related to U.S. patent application Ser. Nos. 11/747,862; 11/747,867; 12/480,929; 12/480,256; 12/483,174; 12/482,640; 12/505,326; and Ser. No. 12/505,335. The present application is also related to U.S. Provisional Patent Application Nos. 61/110,905; 61/115,403; 61/148,809; 61/109,873; 61/109,875; 61/109,879; 61/109,881; 61/109,882; 61/109,889; 61/109,893; and 61/254,997. Each of the U.S. patent applications and U.S. Provisional patent applications listed above is incorporated in its entirety herein by reference.

BACKGROUND OF THE INVENTION

1. Field of the Invention

The present application generally relates to systems and methods for creating ablation zones in human tissue. More specifically, the present application relates to systems and methods for mapping tissue and planning ablation paths therein as a treatment for atrial fibrillation of the heart using ultrasound energy.

The condition of atrial fibrillation (AF) is characterized by the abnormal (usually very rapid) beating of the left atrium of the heart which is out of synch with the normal synchronous movement ('normal sinus rhythm') of the heart muscle. In normal sinus rhythm, the electrical impulses originate in the sino-atrial node ('SA node') which resides in the right atrium. The abnormal beating of the atrial heart muscle is known as 'fibrillation' and is caused by electrical impulses originating instead at points other than the SA node, for example, in the pulmonary veins (PV).

There are pharmacological treatments for this condition with varying degree of success. In addition, there are surgical interventions aimed at removing the aberrant electrical pathways from PV to the left atrium ('LA') such as the 'Cox-Maze III Procedure'. This procedure has been shown to be 99% effective but requires special surgical skills and is time consuming. Thus, there has been considerable effort to copy the Cox-Maze procedure using a less invasive percutaneous catheter-based approach. Less invasive treatments have been developed which involve use of some form of energy to ablate (or kill) the tissue surrounding the aberrant focal point where the abnormal signals originate in PV. The most common methodology is the use of radio-frequency ('RF') electrical energy to heat the muscle tissue and thereby ablate it. The aberrant electrical impulses are then prevented from traveling from PV to the atrium (achieving the 'conduction block') and thus avoiding the fibrillation of the atrial muscle. Other energy sources, such as microwave, laser, and ultrasound have been utilized to achieve the conduction block. In addition, techniques such as cryoablation, administration of ethanol, and the like have also been used. Some of these methods and devices are described below.

There has been considerable effort in developing catheter based systems for the treatment of AF using radiofrequency (RF) energy. One such method includes a catheter having distal and proximal electrodes at the catheter tip. The catheter can be bent in a coil shape, and positioned inside a pulmonary vein. The tissue of the inner wall of the PV is ablated in an attempt to kill the source of the aberrant heart activity.

Another source used in ablation is microwave energy. One such intraoperative device consists of a probe with a malleable antenna which has the ability to ablate the atrial tissue.

Still another catheter based method utilizes the cryogenic technique where the tissue of the atrium is frozen below a temperature of −60 degrees C. This results in killing of the tissue in the vicinity of the PV thereby eliminating the pathway for the aberrant signals causing the AF. Cryo-based techniques have also been a part of the partial Maze procedures described above. More recently, Dr. Cox and his group have used cryoprobes (cryo-Maze) to duplicate the essentials of the Cox-Maze III procedure.

More recent approaches for the treatment of AF involve the use of ultrasound energy. The target tissue of the region surrounding the pulmonary vein is heated with ultrasound energy emitted by one or more ultrasound transducers. One such approach includes a catheter distal tip portion equipped with a balloon and containing an ultrasound element. The balloon serves as an anchoring means to secure the tip of the catheter in the pulmonary vein. The balloon portion of the catheter is positioned in the selected pulmonary vein and the balloon is inflated with a fluid which is transparent to ultrasound energy. The transducer emits the ultrasound energy which travels to the target tissue in or near the pulmonary vein and ablates it. The intended therapy is to destroy the electrical conduction path around a pulmonary vein and thereby restore the normal sinus rhythm. The therapy involves the creation of a multiplicity of lesions around individual pulmonary veins as required.

Yet another catheter device using ultrasound energy includes a catheter having a tip with an array of ultrasound elements in a grid pattern for the purpose of creating a three dimensional image of the target tissue. An ablating ultrasound transducer is provided which is in the shape of a ring which encircles the imaging grid. The ablating transducer emits a ring of ultrasound energy at 10 MHz frequency.

In all above approaches, the inventions involve the ablation of tissue inside a pulmonary vein or of the tissue at the location of the ostium. This may require complex positioning and guiding of the treatment devices to the target site. The ablation is achieved by means of contact between the device and the tissue. Therefore, it would be advantageous to provide an ablation system that does not require such precise positioning and tissue contact and that can create a conduction block in the atrium adjacent the pulmonary vein or around a plurality of pulmonary veins in a single treatment. Moreover, it would be desirable to provide a device and methods of ablation where three dimensional movement of the tip is controlled such that one can create a contiguous lesion in the tissue of desired shape in the wall of the chamber, e.g. the atrium of the heart. Furthermore, the movement of the ultrasound beam is controlled in a manner such that the beam is presented to the target tissue substantially at a right angle to maximize the efficiency of the ablation process. It would also be desirable to provide an ablation system that is easy to use, easy to manufacture and that is lower in cost than current commercial systems.

Furthermore, when delivering energy to tissue, in particular when ablating tissue with ultrasound to treat atrial-fibrillation, the doctor or operator must insure proper alignment of the energy-delivering device. If the transducer is too far away, the ultrasound energy reaching the tissue will not be enough to create a transmural lesion. If the transducer is too close, the ultrasound energy may damage the tissue or cause the transducer of the ultrasound device to overheat. Other factors such as incident angle of the beam and tissue thickness further complicate the task of ablating tissue. Thus, there is a need for systems and methods that provide a user interface during tissue ablation. It would be desirable if such user interfaces provided an anatomical map of the tissue to be ablated that can be used to visually characterize the tissue and also that can be used to help plan an ablation path in the tissue. At least some of these challenges are met by the systems and methods described below.

2. Description of Background Art

Patents related to the treatment of atrial fibrillation include, but are not limited to the following: U.S. Pat. Nos. 6,997,925; 6,996,908; 6,966,908; 6,964,660; 6,955,173; 6,954,977; 6,953,460; 6,949,097; 6,929,639; 6,872,205; 6,814,733; 6,780,183; 6,666,858; 6,652,515; 6,635,054; 6,605,084; 6,547,788; 6,514,249; 6,502,576; 6,416,511; 6,383,151; 6,305,378; 6,254,599; 6,245,064; 6,164,283; 6,161,543; 6,117,101; 6,064,902; 6,052,576; 6,024,740; 6,012,457; 5,405,346; 5,314,466; 5,295,484; 5,246,438; and 4,641,649.

Patent Publications related to the treatment of atrial fibrillation include, but are not limited to International PCT Publication No. WO 99/02096; and U.S. Patent Publication No. 2005/0267453.

Scientific publications related to the treatment of atrial fibrillation include, but are not limited to: Haissaguerre, M. et al., Spontaneous Initiation of Atrial Fibrillation by Ectopic Beats Originating in the Pulmonary Veins, New England J. Med., Vol. 339:659-666; J. L. Cox et al., The Development of the Maze Procedure for the Treatment of Atrial Fibrillation, Seminars in Thoracic & Cardiovascular Surgery, 2000; 12: 2-14; J. L. Cox et al., Electrophysiologic Basis, Surgical Development, and Clinical Results of the Maze Procedure for Atrial Flutter and Atrial Fibrillation, Advances in Cardiac Surgery, 1995; 6: 1-67; J. L. Cox et al., Modification of the Maze Procedure for Atrial Flutter and Atrial Fibrillation. II, Surgical Technique of the Maze III Procedure, Journal of Thoracic & Cardiovascular Surgery, 1995; 110:485-95; J. L. Cox, N. Ad, T. Palazzo, et al. Current Status of the Maze Procedure for the Treatment of Atrial Fibrillation, Seminars in Thoracic & Cardiovascular Surgery, 2000; 12: 15-19; M. Levinson, Endocardial Microwave Ablation: A New Surgical Approach for Atrial Fibrillation; The Heart Surgery Forum, 2006; Maessen et al., Beating Heart Surgical Treatment of Atrial Fibrillation with Microwave Ablation, Ann Thorac Surg 74: 1160-8, 2002; A. M. Gillinov, E. H. Blackstone and P. M. McCarthy, Atrial Fibrillation: Current Surgical Options and their Assessment, Annals of Thoracic Surgery 2002; 74:2210-7; Sueda T., Nagata H., Orihashi K., et al., Efficacy of a Simple Left Atrial Procedure for Chronic Atrial Fibrillation in Mitral Valve Operations, Ann Thorac Surg 1997; 63:1070-1075; Sueda T., Nagata H., Shikata H., et al.; Simple Left Atrial Procedure for Chronic Atrial Fibrillation Associated with Mitral Valve Disease, Ann Thorac Surg 1996; 62:1796-1800; Nathan H., Eliakim M., The Junction Between the Left Atrium and the Pulmonary Veins, An Anatomic Study of Human Hearts, Circulation 1966; 34:412-422; Cox J. L., Schuessler R. B., Boineau J. P., The Development of the Maze Procedure for the Treatment of Atrial Fibrillation, Semin Thorac Cardiovasc Surg 2000; 12:2-14; and Gentry et al., Integrated Catheter for 3-D Intracardiac Echocardiography and Ultrasound Ablation, IEEE Transactions on Ultrasonics, Ferroelectrics, and Frequency Control, Vol. 51, No. 7, pp 799-807.

BRIEF SUMMARY OF THE INVENTION

The present application generally relates to systems and methods for creating ablation zones in human tissue. More specifically, the present application relates to systems and methods for anatomically mapping tissue and planning ablation paths therein as a treatment for atrial fibrillation of the heart using ultrasound energy. The term map as used herein will generally refer to an anatomical map of the tissue and adjacent regions. The map is not intended to be a recommendation of therapy, but merely an anatomical map of tissue characteristics and/or ablation device position relative to the tissue. The physician decides where to apply the ablation therapy.

In a first aspect of the present invention, a method for ablating tissue in a patient having atrial fibrillation comprises advancing an elongate flexible shaft through a patient's vasculature into a chamber of a heart. The elongate flexible shaft has a proximal end, a distal end, an energy source and a sensor. The energy source and the sensor are disposed near the distal end of the shaft. Tissue in the heart is scanned with the sensor and data about the tissue is captured. The captured data may be grouped into one of a plurality of tissue classifications and an anatomical map of the tissue showing aspects of the grouped data is displayed. At least a portion of the tissue is ablated so as to form a conduction block that blocks aberrant electrical pathways in the heart. The ablated tissue is grouped into one or more predefined tissue classifications prior to ablation thereof.

The method may further comprise transseptally crossing an atrial septum of the heart with the flexible shaft. The advancing step may comprise positioning at least a portion of the flexible shaft into a left atrium of the heart.

The scanning step may comprise emitting a beam of ultrasound energy from the energy source and capturing the energy reflected back from the tissue with the sensor. The energy source may comprise an ultrasound transducer, and the sensor may comprise the ultrasound transducer. The scanning step may comprise scanning the tissue in a raster pattern by moving the distal tip of the catheter. The data may comprise distance between the sensor and a surface of the tissue. The data may comprise the position of the distal end of the catheter and the distance between the sensor and the tissue surface, as well as one or more of tissue thickness, tissue type, identification of collateral tissue, lesion depth, presence of electrical signals, and tissue motion.

The method may further comprise transmitting the data to a processor, processing the data, and storing the processed data. The displaying step may comprise displaying the processed data. The capturing step may comprise receiving tissue information with the sensor. The grouping step may comprise categorizing the data into an "ablation" category and a "non-ablation" category. The "ablation" category may consists of the tissue having captured data falling into a pre-defined desired range of values, and the "non-ablation" category may consist of the tissue having captured data outside of the pre-desired range of values. The grouping step may further comprise categorizing the data into a "borderline" category, wherein the data in the "borderline" category consists of the data falling between the "ablation" and the "non-ablation" categories. The grouping step may comprise categorizing the data into a gradient of classifications.

The displaying step may comprise displaying a graphical representation of the tissue scanned. The graphical representation may comprise a two dimensional or a three dimensional topographical representation of the tissue. The graphical representation may visually indicate regions of the tissue suitable for ablation and regions of the tissue that are unsuitable for ablation. The suitable regions for ablation may consist of those regions having a gap between the tissue and the sensor ranging from 1 mm to 20 mm. The unsuitable regions for ablation may consist of those having a gap greater than 22 mm. The graphical representation may visually indicate borderline regions of the tissue that may be suitable for ablation. The borderline regions may consists of those having a gap between the tissue and the sensor less than 1 mm, or the gap may be in the range from greater than 18 mm to less than 22 mm. The graphical representation may visually indicate motion of the tissue as the heart expands and contracts, or the graphical representation may comprise two or more characteristics of the tissue. The graphical representation may comprise characteristics of the tissue in real time, or in close to real time, refreshing for example, every 20 seconds.

The energy source may comprise an ultrasound transducer, and the ablating step may comprise directing a beam of ultrasound energy from the energy source. The method may further comprise identifying anatomical structures adjacent the tissue such as one or more pulmonary veins in the left atrium of the heart. The method may further comprise re-scanning the tissue with the sensor and capturing additional data about the tissue. The method may also comprise determining whether the anatomical map is satisfactory. The map may be updated during the ablation step.

In another aspect of the present invention, a method of ablating tissue in a patient as a treatment for atrial fibrillation comprises planning an initial ablation path in the tissue and verifying that the initial ablation path is acceptable. Excluded zones in the initial ablation path are displayed so that the initial ablation path may be revised in order to avoid the excluded zones. The tissue is then ablated along the revised ablation path.

The planning step may comprise graphically planning the initial ablation path on an anatomical map of the tissue. The map may comprise a two dimensional or a three dimensional representation of the tissue. Planning may comprise providing user input into an ablation system with an input device. Planning may comprise drawing the initial ablation path on a map of the tissue, or planning may comprise selecting, positioning, scaling, and rotating, or otherwise editing a shape overlaid on an anatomical map of the tissue. The shape may comprise one of a spot, a line, an ellipse, a circle, a figure eight, and a rectangle. Planning may comprise defining a center point and setting a shape dimension around the center point for the initial ablation path. The shape dimension may comprise a circle with a radius extending from the center point. An operator may define tissue that is suitable for the initial ablation path, and an ablation system may automatically determine the initial ablation path passing therethrough. An operator may also define tissue that is unsuitable for the initial ablation path, and the initial ablation path does not pass through the unsuitable tissue. The planning may comprise considering one of gap distance between a sensor and a surface of the tissue, thickness of the tissue, motion of the tissue, tissue type, tissue angle, and electrical signals in the tissue.

The verifying step may comprise comparing tissue data with predetermined acceptance criteria. The tissue data may comprise one of gap distance between a sensor and a surface of the tissue, thickness of the tissue, motion of the tissue, type of the tissue, and angle of the tissue. The displaying step may comprise displaying regions of the tissue that are suitable for ablation, regions of the tissue that are not suitable for ablation, and regions of the tissue that may not be suitable for ablation.

The revising step may comprise altering the initial ablation path to avoid regions of the tissue that should not be ablated. The revising step may also comprise redrawing the initial ablation path, or detouring the initial ablation path to avoid excluded zones. The revising step may comprise one of altering dwell time of an energy beam, changing the energy beam density, modifying lesion depth, and changing gap distance between a sensor and the surface of the tissue. The ablating step may comprise directing energy from an energy source and sensing energy reflected from the tissue with a sensor. The energy source may comprise an ultrasound transducer and the directed energy comprises a beam of ultrasound energy.

The ablation step may comprise the step of sensing tissue data with an ablation system and relying on the system to modify aspects of ablation based on the sensed data. Modified aspects may comprise changing dwell time, energy beam density, or changing gap distance.

These and other embodiments are described in further detail in the following description related to the appended drawing figures.

DETAILED DESCRIPTION OF THE INVENTION

The following description is not intended to limit the invention to these exemplary embodiments, but rather to enable any person skilled in the art to make and use this invention.

Figure 1:
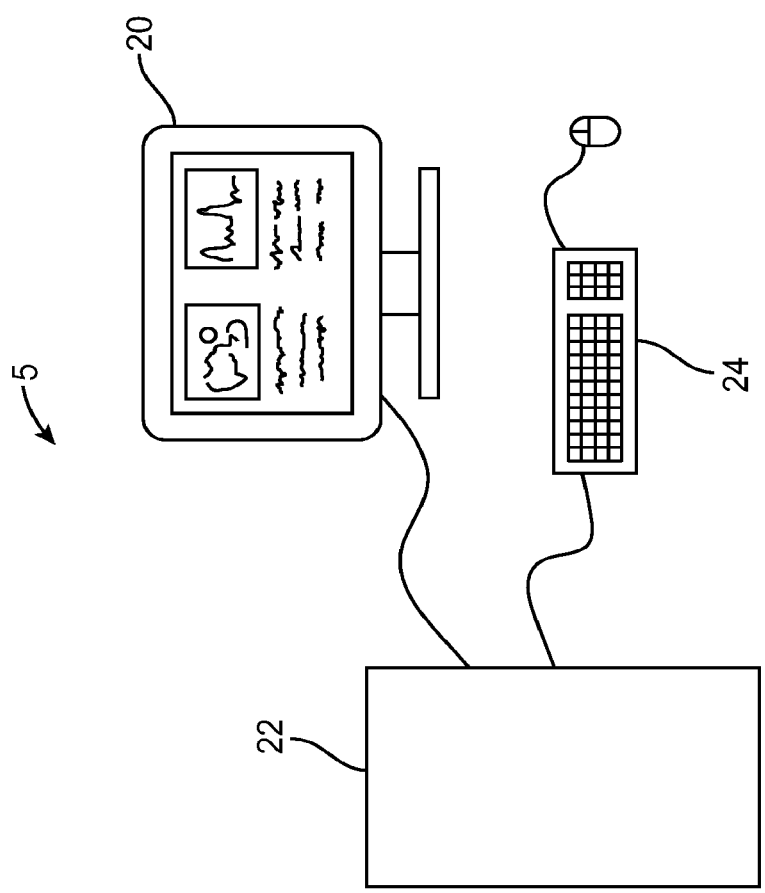
FIG. 1 illustrates an exemplary embodiment of an ablation system.
Figure 1:
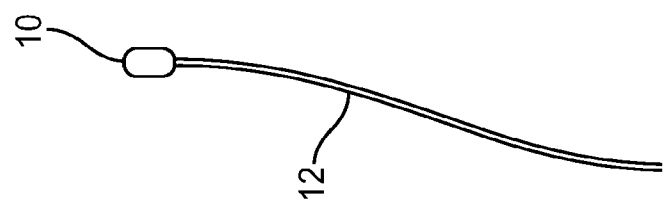

FIG. 1 shows an exemplary system for acquiring and representing tissue information as well as planning an ablation path in the tissue. The system is preferably used to guide a user during an operation, in particular during ablation of heart tissue for the treatment of atrial fibrillation. The preferred embodiments also include a user interface to present the data in an understandable format. While the system, method, and user interface have been designed for the treatment of atrial fibrillation, the system and method may alternatively be used in any suitable situation such a treating other arrhythmias as well as anatomically mapping and heating or ablating other tissues in the body.

The System. Referring to FIG. 1, the system 5 of the preferred embodiment includes an energy delivery and sensing device 10 to sense properties of the tissue, a catheter 12 to act as a channel to position and control the energy delivery and sensing device 10, an external processor 22 to interface the energy delivery and sensing device 10 with user input and output devices, a display 20 to visually depict the tissue data to the user, and an input device 24 to receive commands from a user. Additional details on the system 5 are disclosed in U.S. Provisional Patent Application No. 61/254,997 previously incorporated by reference, as well as other Provisional and Non-Provisional patent applications previously incorporated herein by reference.

The energy delivery and sensing device 10 of the preferred embodiment functions to sense properties of the tissue and deliver energy thereto. The energy delivery and sensing device 10 additionally functions to ablate tissue (to create a substantially transmural lesion in the tissue). Preferably, the energy delivery and sensing device 10 uses ultrasound for ablation and sensing of tissue. To ablate tissue, high-energy ultrasound is preferably used in creating the lesion at a localized spot. To sense tissue, low-energy ultrasound and the echo of the ultrasound off tissue are preferably used to sense tissue characteristics such as a gap distance (the distance between the energy delivery and sensing device 10 and the surface of the tissue). Tissue thickness, tissue motion, tissue type, tissue angle, lesion depth, and/or any suitable characteristic may alternatively be sensed. Alternatively, the energy delivery and sensing device 10 may use any suitable device or combination of devices for the ablation and sensing of tissue.

The catheter 12 of the preferred embodiment functions to act as a channel to position and control the energy delivery and sensing device 10. The catheter 12, as is well known in the art, preferably includes a tube able to be threaded through a blood vessel into a chamber of the heart. Any suitable alternative may be used to position and control the energy delivery and sensing device 10. The energy delivery and sensing device 10 is preferably attached to the distal end of the catheter 12. The catheter 12 preferably has an electrical connection running along the length of tube. The electrical connection preferably connects the energy delivery and sensing device with outside electrical devices. Alternatively, a connection may be formed wirelessly or in any suitable way.

Figure 5A:
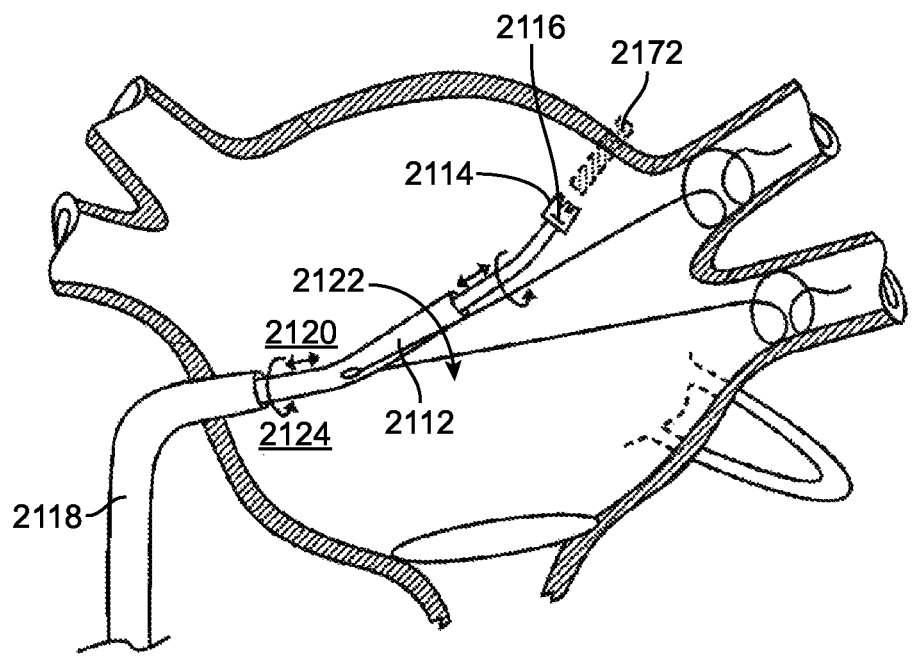
FIG. 5A shows a catheter device positioned in the left atrium of the heart.

Referring to the embodiment of FIG. 5A, catheter 2112 has three independent movements available. First, the catheter 2112 can move axially in the guide tube 2118 as depicted by 2120. The distal tip of the catheter 2112 is equipped to be bent in a manner 2122. Finally, the catheter 2112 can be rotated in the guide sheath 2118 in a manner 2124.

Figure 5B:
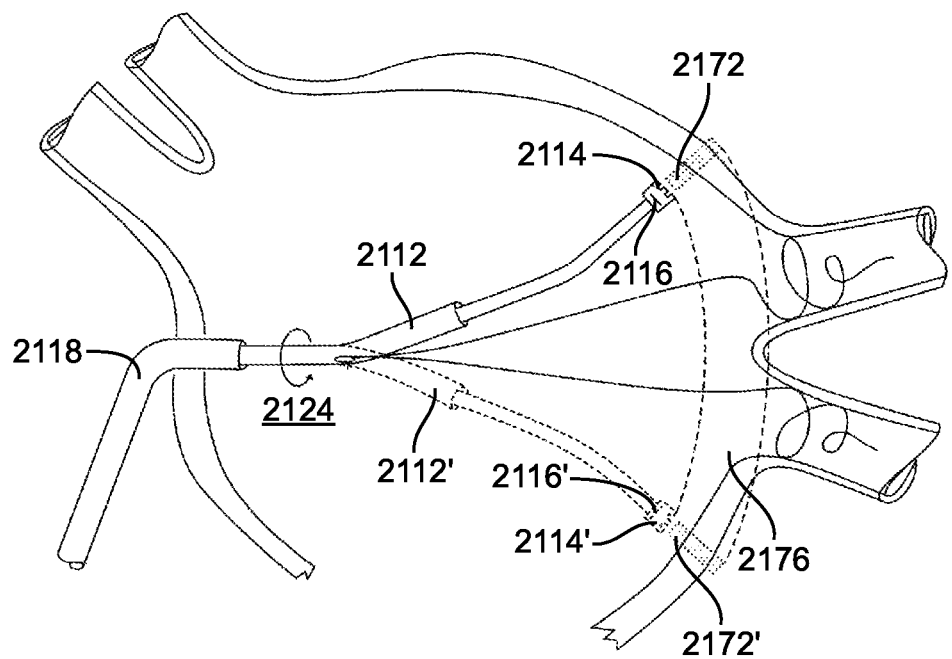
FIG. 5B shows the use of the device of FIG. 5A in the atrium of the heart.

FIG. 5B shows the positions of the catheter elements in the left atrium. The ultrasound element 2116 in the housing 2114 emits an ultrasound beam to establish an ablation window 2172. Now, as the outer catheter 2112 is rotated inside the guide sheath 2118 in the manner 2124, the ultrasound beam 2172 sweeps a generally circular path 2176 creating a section of a conical shell.

The external processor 22 of the preferred embodiment functions to interface the energy delivery and sensing device 10 with user input and output devices. The external processor 22 preferably receives data from the energy delivery and sensing device 10 and manages the content displayed on a monitor. The external processor additionally functions to process tissue data, store tissue data, control the energy delivery and sensing system 10, or any other suitable actions regarding interfacing with the energy delivery and sensing device 10. The external processor 22 is preferably a personal desktop, laptop computer, or embedded computer, but may alternatively be any suitable device. The external processor contains all hardware and firmware required to implement ultrasound signal transmission and reception.

The display 20 of the preferred embodiment functions to visually depict the tissue data to the user. The display 20 is preferably a computer monitor or alternatively, any suitable display device may be used.

The input device 24 of the preferred embodiment functions to receive commands from a user. The input device 24 is preferably a keyboard and mouse. The input device 24 may alternatively be a touch screen integrated into the display 20, a specialized controller, foot pedals, a stylus, or any suitable device for receiving user commands.

Figure 2:
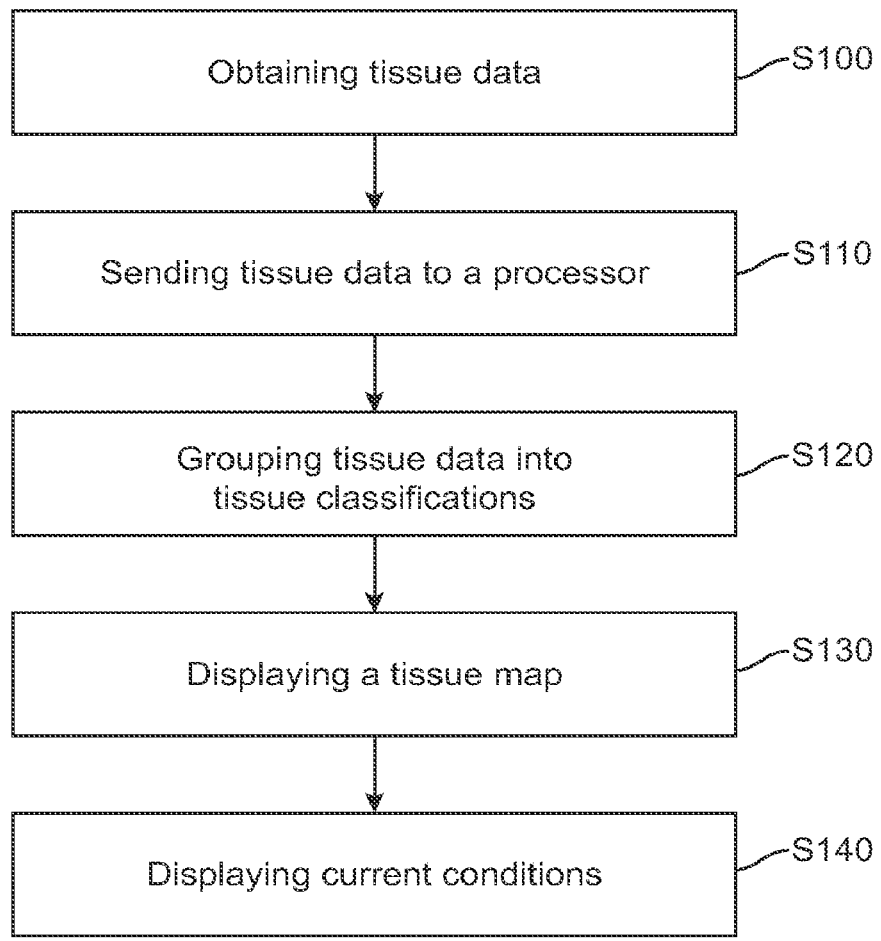
FIG. 2 illustrates an exemplary method of providing a user interface for cardiac ablation.

Method of Providing a User Interface for Cardiac Ablation. As shown in FIG. 2, the method of providing a user interface for cardiac ablation includes step S100 where the catheter tip is moved in order to scan the tissue and capture data; step S110 of sending tissue data to a processor to prepare the tissue data for signal processing; step S120 of storing, and displaying grouping tissue data into tissue classifications to analyze the data for particular ranges of characteristics; step S130 of displaying a tissue map to present the tissue data to a user; and step S140 of displaying current conditions to provide real time data for currently interrogated tissue. The method of displaying a user interface for cardiac ablation preferably provides the information relevant to the tissue ablation process in a graphical manner.

Step S100, which recites moving the catheter tip, functions to scan a surface of heart tissue and capture data. Step S100 is preferably accomplished by a catheter and energy delivery device and, more preferably, the catheter device of system 5 as described above. The energy delivery system includes an ultrasound transducer for ablation and sensing of heart tissue, although any suitable sensor may be used. The energy delivery system preferably rasters across the surface of the heart tissue gathering gap data. Gap data is preferably a set of data points correlating position with gap distance (the distance between the sensor and tissue surface). The energy delivery system may alternatively sense tissue thickness, tissue type, collateral tissue, lesion depth, electrical signals, tissue motion, or any suitable tissue characteristic.

Step S110, which recites sending tissue data to a processor, functions to prepare the tissue data for signal processing, storing, and/or displaying. The tissue data is preferably sent through a wired connection within the catheter, but may alternatively be sent wirelessly or by any suitable means. The processor is preferably an external processor (i.e. not part of the catheter device), and more preferably, the processor is a personal desktop or laptop computer or any suitable processor. The external processor functions to perform signal processing on the tissue data, organize the tissue data, store the tissue data, manage the display, interface with input devices, and/or any other suitable tasks. The tissue data is preferably raw data (unprocessed) that has been collected from the catheter device, but may alternatively and/or additionally be processed by an internal processor of the catheter device.

Step S120, which recites grouping tissue data into tissue classifications, functions to analyze the data for particular ranges of characteristics. Preferably, the tissue data is grouped into categories of 'ablation tissue' and 'non-ablation tissue'. Ablation tissue is preferably any tissue that falls within a range of ideal conditions for proper ablation. The conditions may include a desired range of gap distances, tissue thickness, tissue type, collateral tissue, lesion depth, electrical signals, tissue motion, and/or any suitable characteristic, and the range of values are preferably selected to ensure a transmural lesion without collateral damage to neighboring tissue or the device. Non-ablation tissue is preferably any tissue that should not be ablated under normal circumstances. The non-ablation tissue has tissue characteristics that are outside the desired range of gap distances, tissue thickness, tissue type, lesion depth, electrical signal level, tissue motion, and/or any suitable characteristic. Non-ablation tissue is preferably any area of tissue where ablation should not be performed or where ablation is not recommended. There may be an additional tissue classification for 'borderline ablation tissue'. Borderline ablation tissue is preferably any tissue that has tissue characteristics that are in-between ablation tissue characteristics and non-ablation tissue characteristics. Borderline ablation tissue functions as a warning tissue classification (ablation may be performed but is not fully desired). Alternatively, any suitable classifications may be used when grouping the tissue data including but not limited to a gradient of classifications that is substantially similar to an analog scale. The gradient of classifications is preferably a range of optimum characteristics where 100% represents the optimal tissue characteristics and o % represents tissue that should not be ablated under any condition. The gradient of classifications may alternatively represent any suitable scale. In an alternative version, a plurality of tissue classifications for each area of tissue may be used. In this alternative version, an area of tissue may include individual tissue classifications for categories of gap distances, tissue thickness, tissue type, collateral tissue, lesion depth, electrical signals, tissue motion, and/or any suitable tissue characteristic. The plurality of tissue classifications may include tissue classifications with 'ablation tissue'/'non-ablation tissue' classification, gradient of classifications, or any suitable type or combination of classifications. The individual tissue classifications function to provide more specific groupings so the cause of a warning is known. Additionally, the tissue characterizations may be tied to the movement of the heart during its contraction and relaxation. This may be accomplished by monitoring and recoding an electrocardiogram while the tissue data is collected. Thus, the tissue map may be presented at any phase of the heart's pumping cycle.

Step S130, which recites displaying tissue map, functions to present the tissue data to a user. The tissue map is preferably a graphical representation of the surface of heart tissue scanned during Step S100 but could also be a conventional ultrasound image of the tissue. In a first version, the tissue map is a 2D graphical representation of the surface contours of the tissue. The 2D graphical representation is preferably calculated using gap data collected during Step S100 and is represented by a topographical image using colors, shading, contour lines, or any suitable means to represent the 3D surface qualities of the tissue. The 2D representation may alternatively be created using tissue angle data or any suitable tissue characteristic.

In a second version of Step S130, the tissue map is a 3D model represented in a surface or solid based 3D computer graphic image. The 3D graphical representation is preferably calculated using gap data collected during Step S100 or using any suitable tissue characteristic. The 3D model functions to provide a realistic representation of the tissue surface. The 3D model may additionally be rotated for viewing the tissue surface from different perspectives. Additionally, shading tissue classification regions may be performed during Step S120. The tissue classifications from Step S120 are preferably used to shade the regions of tissue to represent where ablation may occur and where it should not on the tissue map. A green shaded region preferably represents an ablation tissue candidate. A yellow shaded region preferably represents a borderline ablation tissue candidate. A red shaded region preferably represents the tissue region to be excluded from ablation (e.g. collateral tissue such as the esophagus or phrenic nerve), and a blue shaded region preferably represents tissue that is too far away from the ablation device and therefore is tissue that is also not a candidate for ablation. Any suitable shading for the tissue classifications may be used to represent any suitable tissue classifications.

In a third version of Step S130, the tissue map is a graphical representation of the tissue motion. Preferably, tissue motion is represented as a scrolling graph with time on an x-axis and gap distance in millimeters on a y-axis. The graph preferably displays the current gap distance and previous gap distances over the past 5 seconds or any suitable time span. Additionally, signal frequency, period, maximum variance, average variance, or any suitable numerical data calculated from the tissue data may be displayed alongside the graph or color coded and superimposed on the tissue map. The time position graph may have a color-coded y-axis, the gap distance axis. The y-axis displacement values preferably range from 0-30 mm, and the axis has a color-coded regions. A green section preferably represents a suitable gap distance (1-20 mm), while yellow preferably represents a borderline gap distance (0-1 mm and 18-22 mm), and blue represents an out-of-range gap distances (greater than 22 mm). A red section preferably represents collateral tissue that is to be excluded from ablation. The values may be any suitable gap distance ranges and colors may be any suitable color combinations. The graph preferably has horizontal bars extending across the graph that function to clarify for the user to see if the motion of the tissue will cause the gap distance to be over or under a suitable gap distance.

In a fourth version of Step S130, the tissue map is a combination of varying tissue maps either to be displayed at the same time, or from which to be selected. The combination of varying tissue maps functions to provide a multitude of ways to understand the data.

Additionally, the method of providing a user interface for cardiac ablation of the preferred embodiment includes displaying current conditions S140. Displaying the current conditions functions to provide real time data for currently interrogated tissue (the tissue the energy delivery and sensing device is directly above). The current conditions are preferably the gap distances, tissue thickness, tissue type, collateral tissue, lesion depth, electrical signals, tissue motion, and/or any suitable tissue characteristic. The current conditions are preferably displayed at the same time the tissue map is displayed. The current conditions are preferably represented as numerical values. The current conditions may alternatively and/or additionally be represented by a graphic, a bar graph, a virtual dial, or any suitable display to communicate the current conditions.

Figure 3:
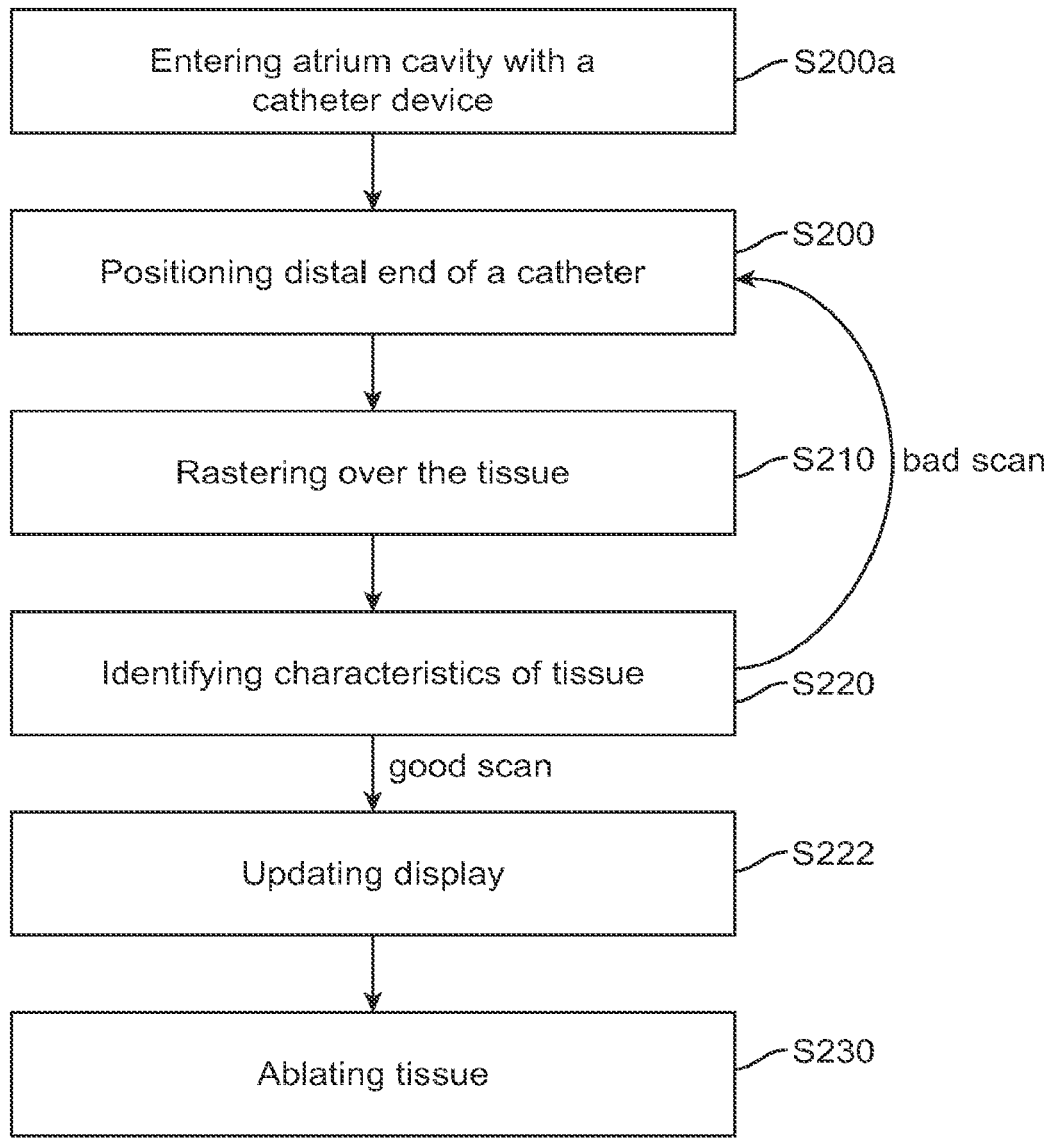
FIG. 3 illustrates an exemplary method of the mapping process.

Method for Mapping and Ablating Tissue. As shown in FIG. 3, the preferred method for mapping and ablating tissue includes step S200a of entering the atrium cavity with a catheter device; step S200 of positioning the distal end of a catheter; step S210 of rastering over the tissue; step S220 of identifying characteristics of tissue; step S222 of updating display S222; and step S230 of ablating tissue.

Step S200a, which recites entering the atrium cavity with a catheter device and step S200 of positioning the distal end of a catheter, functions to position the catheter device within a chamber of the heart. The catheter device is preferably a catheter with an energy delivery and sensor device located on the distal end. More preferably, the catheter device is identical to system 5 as described above. The catheter device preferably pierces through the septum, and the distal end of the device is positioned within the left atrium of the heart. A wire guide is additionally positioned in the pulmonary vein or suitable structure to act as an anchor during the rastering and ablation process.

Step S210, which recites rastering over the tissue, functions to systematically move the energy delivery and sensing device over the surface of tissue to gather tissue data. The pattern of rastering is preferably a linear zig-zag pattern, but may alternatively be a spiral or any suitable pattern that covers the tissue. Additionally, the pattern of rastering may be altered during the step, once an orientation has been established. Altering the raster process functions to increase efficiency and help approximate the ideal positioning of the energy delivery and sensing device. The energy delivery and sensing device preferably collects tissue data continuously, periodically, or at any suitable time during the rastering process.

Step S220, which recites identifying characteristics of tissue, functions to process the tissue data and judge the quality of the scan. The tissue data is preferably signal-processed to identify anatomical structures. For example, the pulmonary veins are identified in the gap data of the tissue data; the pulmonary veins may be identified as large gap distances at the site of the ostium of the pulmonary vein. Alternatively, the tissue motion, electrical activity, tissue angle, tissue thickness, or any suitable tissue characteristic may be signal processed. Identified anatomical structures function to orientate the catheter device within the heart chamber. If the correct anatomical structures have been identified, the method proceeds to ablate the tissue. If the anatomical structures are identified incompletely or no structures are identified, then step S210, rastering over the tissue, is repeated by targeting the raster over a different tissue region. Additionally, the rastering pattern may be changed from the previous time.

In an alternative version of step S220, the user is provided with an interface for deciding if the tissue data is satisfactory. The tissue data is preferably represented graphically on a display. The user preferably analyzes the representation of tissue data and selects the provided options of 're-scan' or 'proceed'. Any suitable options may alternatively be provided. The user may additionally select a region to rescan.

Once the tissue has been mapped, an ablation path may be planned. Additional details regarding planning an ablation path are disclosed below. Step S230, which recites ablating tissue, functions to form a substantially transmural lesion around the source of the atrial fibrillation. Ablation preferably occurs to tissue surrounding the source of the atrial fibrillation, and excludes collateral tissue. The ablation of tissue is preferably guided by input from the user, but may alternatively be an automated or partially automated process.

The method for mapping and ablating tissue of the preferred embodiment additionally includes the step S222 of updating a display. Step S222 preferably occurs before and/or during the ablation process. Updating a display functions to present the user with a representation of the tissue data. The updating of the display is preferably similar to steps from the method of providing a user interface for cardiac ablation, as described above.

Figure 4:
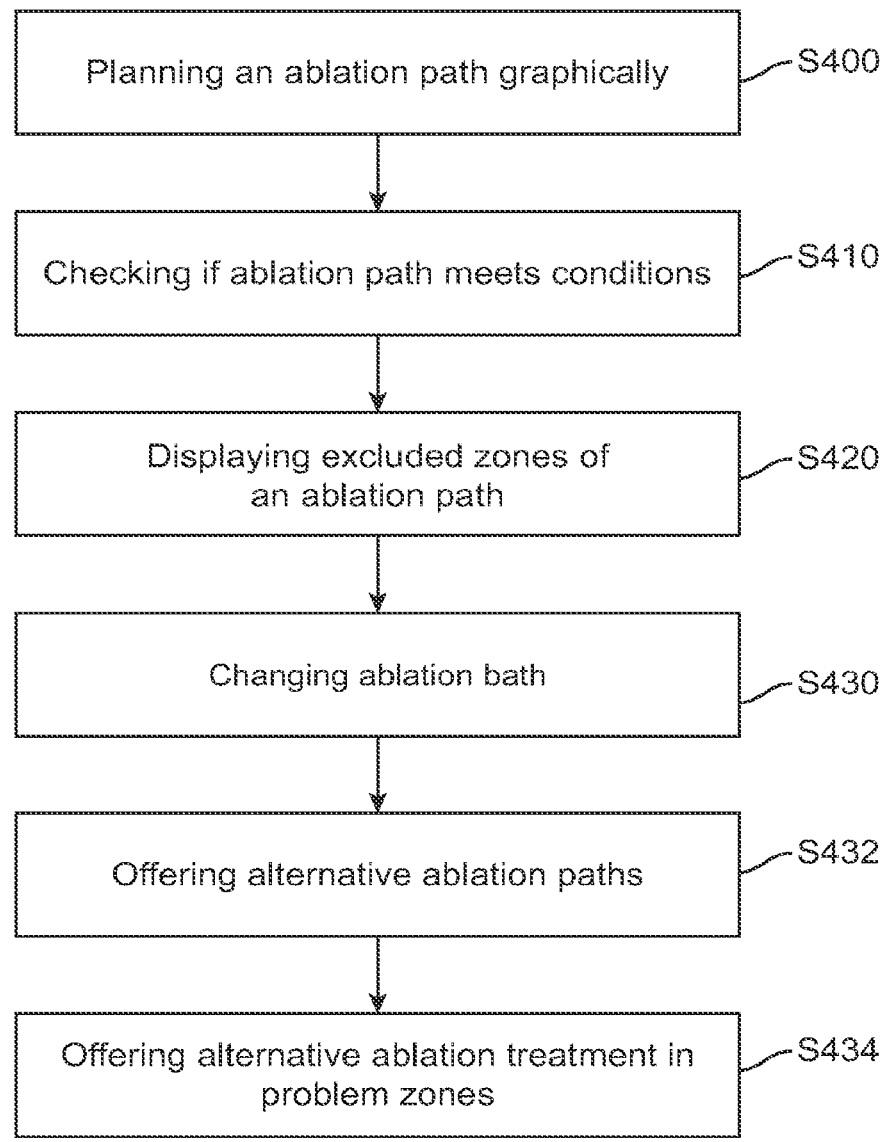
FIG. 4 illustrates an exemplary method of planning an ablation path.

Method for Planning an Ablation Path. As shown in FIG. 4, the preferred method for planning an ablation path includes the step S400 of planning an ablation path graphically; the step S410 of checking if the ablation path meets particular conditions; the step S420 of displaying excluded zones of an ablation path; and the step S430 of changing an ablation path if necessary. The method of planning an ablation path functions to provide an easy to use interface with which a user may sketch, check, and modify an ablation path. The method further functions to provide a set of conditions ensuring proper ablation of tissue.

Step S400, which recites planning an ablation path graphically, functions to allow a user to plan an ablation path overlaid directly on a tissue map (a graphical anatomical representation of the tissue surface). The tissue map preferably indicates the 3D surface qualities of the heart tissue, and may be a 2D image, a 3D computer graphic, or any suitable representation of the tissue. The tissue map is preferably displayed on a computer display, and a keyboard, a stylus or a mouse provide an interface for a user to interact with the display. A touch screen, specialized control panel, or any suitable interface providing input and a form of communication output may alternatively be used.

In a first version of step S400, the planning of an ablation path preferably includes drawing a shape on a tissue map. The shape is preferably drawn on the tissue map by using a mouse or a stylus to trace the ablation path. Additionally, an external processor may perform auto correction, smoothing, or any suitable alterations of the drawn shape. Additionally, any drawing of a shape may be projected or overlaid onto the surface of the tissue to reflect where the actual ablation will occur. This addition functions to make the drawing process reflect where the tissue will be ablated. A shape may also be transformed so that the ablation path on the 3D tissue surface more closely corresponds to the shape drawn on a 2D representation. In alternative embodiments, the user can select an ablation path from a library containing several predefined ablation paths.

In a second version of Step S400, the planning of an ablation path preferably includes selecting, positioning, scaling, and rotating a shape overlaid on a tissue map to define the ablation path. Preferably, the shape is an outline of an ellipse, but alternatively, the shape may be a spot, a line, a circle, a figure eight, a rectangle, or any regular or irregular shape that may be suitable for an ablation path. The shape is preferably positioned, scaled, and rotated as is commonly used in computer graphics programs. Additionally, multiple shapes may be used. The outer most outline of the combined multiple shapes is preferably used as the ablation path, but alternatively, any rule may define where the ablation path lies for multiple shapes.

In a third version of step S400, the planning of an ablation path preferably includes defining a center point and setting a shape dimension around that center point for the ablation path to occur. The center point is preferably made at the source of the atrial fibrillation. The user may use a mouse or stylus to position the center point, but alternatively the processor may identify the source of atrial fibrillation through analysis of tissue data and then automatically position the center point. The shape dimension preferably defines the radius of a circle centered on the center point, but alternatively the shape dimension may define a dimension of any suitable shape. The shape dimension is preferably set through a dialog box or any suitable interface may be used. As an alternative, multiple center points may be set. Using multiple center points functions to allow multiple sources of atrial fibrillation to be targeted. Each center point preferably has a set shape dimension, and the ablation path is preferably the outline of the shape formed by the union of all the center point shapes.

In a fourth version of step S400, the planning of an ablation path preferably includes defining tissue that is suitable for ablation via a user, and automatically setting an ablation path that passes through the defined tissue via a processor. Preferably, tissue is defined by the user highlighting an area of tissue on a tissue map. The highlighted tissue preferably encircles the source of the atrial fibrillation, and also approximates the desired ablation path. The highlighted tissue is preferably tissue near where the user would prefer the ablation path to occur. Additionally, the user may highlight tissue where ablation should not occur (ablation tissue region) or where ablation of the tissue should be excluded (non-ablation tissue region). The processor automatically forms an ablation path by defining a shape that falls within the highlighted ablation tissue region and not within the highlighted non-ablation tissue region. Alternatively, signal processing of tissue data may be used to automatically define the ablation tissue regions and the non-ablation tissue regions. This alternative functions to provide an automatic way of defining the ablation path. The tissue data may be able to use gap distance, tissue thickness, tissue motion, tissue type, tissue angle, electrical signal, and/or any suitable tissue characteristic to aid in finding an optimum ablation path. Additionally, the tissue data may be used to define a preference map (a map relating to the tissue surface and the preference for ablation occurring at any given point). The preference map functions to use tissue data to provide more detailed information and an easier way to automatically calculate ablation paths. The preference map is preferably used to calculate the optimum ablation path for avoiding non-ablation tissue regions. The preference map is preferably a data structure that preferably approximates the preference for ablating tissue on a gradient scale. One example of a preferred gradient scale is 0%-100% scale which covers the assessment of desirability of ablation based on user judgment, where 0% is for tissue that should not be ablated, 50% for tissue where caution must be used while ablating, and 100% for tissue where ablation can occur with little chance of complications. Any suitable gradient scale may, however, be used.

Step S410, which recites checking if ablation path meets particular conditions, functions to validate tissue characteristics for the criteria of a transmural lesion ablation path. The tissue of the planned ablation path preferably has associated tissue data (measured tissue characteristics). The tissue data is preferably sensed during a sensing scan of the tissue. The tissue data may alternatively be gathered after the ablation path is drawn, and a test pass is performed where the energy delivery and sensing device follows the drawn ablation path and collects tissue data. The tissue data preferably include gap distance, tissue thickness, tissue motion, tissue type, tissue angle, and/or any suitable tissue characteristic for each area of tissue. The tissue data of the ablation path is then compared to predetermined tissue characteristic values. The predetermined tissue characteristics are the preferred ranges of values for tissue ablation. Based on the comparison, tissue is categorized and preferably color coded on a map into different sections. A green section preferably represents tissue suitable for ablation, while yellow preferably represents a borderline area for ablation, and blue represents tissue that is out of range and therefore that is not a candidate for ablation. A red section preferably represents collateral tissue that is to be excluded from ablation. If any segment of the ablation path includes tissue classified as borderline or excluded tissue, then the user is preferably warned. Step S410 is preferably initiated by a button requiring user activation. Step S410 may alternatively automatically occur after Step S400.

Step S420, which recites displaying excluded zones of an ablation path, functions to alert the user to specific issues with the ablation path. The tissue categories of borderline tissue, excluded tissue, and not a candidate for ablation are preferably used in communicating excluded zones or possible exclusion zones. The planned ablation path is preferably colored according to the tissue category, and these zones may additionally flash or any other suitable graphical alteration may be used to make these zones more apparent.

Step S430, which recites changing an ablation path, functions to alter the ablation path to solve specific issues with the planned ablation path. Preferably, Step S430 uses methods similar to those described in Step S400 to alter the ablation path. The user preferably redraws an ablation path avoiding excluded zones. Alternatively, the ablation path may remain the same besides the excluded zones. A detour path may be drawn around the excluded zones using methods described in Step S400 or using any suitable drawing tools.

An additional sub-step of Step S430 includes offering alternative ablation paths S432, that functions to suggest automatically generated ablation paths that resolve any excluded zones. The alternative ablation path preferably avoids any excluded zones, and substantially preserves the ablation path not in excluded zones. Additionally, the alternative ablation path is preferably presented to the user; the user may then approve the alternative ablation path. Multiple alternative ablation paths may alternatively be offered, and the user may select the most suitable one. Additionally, the user may select to ignore the warning and continue with the current ablation path.

Another additional sub-step of step S430 includes altering that ablation treatment in excluded zones S434, that functions to provide a way for tissue to be ablated with special caution when it is near collateral tissue (tissue that should not be damaged during ablation). The excluded zones are preferably selected, and ablation process options are displayed. The options to alter the ablation treatment preferably include dwell time, energy beam intensity, gap distance, lesion depth, and/or any other suitable parameters of the ablation process that may be altered to lessen or strengthen the amount of ablation. Changes to the ablation process preferably only affect the excluded zones. The options may alternatively be predefined settings, presented to the user as 'minimal ablation', 'medium ablation', 'strong ablation', or any suitable presetting.

While the above is a complete description of the preferred embodiments of the invention, various alternatives, modifications, and equivalents may be used. Therefore, the above description should not be taken as limiting in scope of the invention which is defined by the appended claims.

What is claimed is:

1. A method for ablating tissue in a patient having atrial fibrillation, said method comprising:
   advancing an ultrasound transducer through a patient's vasculature into a chamber of a heart;
   emitting ultrasound energy over target tissue in the heart using the ultrasound transducer;
   receiving reflected ultrasound energy reflected off the target tissue using the ultrasound transducer;
   identifying a first portion of the target tissue as ablation tissue based at least in part on the reflected ultrasound energy;

identifying a second portion of the target tissue as non-ablation tissue based at least in part on the reflected ultrasound energy;

generating a tissue-ablation map of the target tissue based at least in part on the reflected ultrasound energy, the tissue-ablation map representing the first portion of the target tissue as ablation tissue and representing the second portion of the target tissue as non-ablation tissue; and ablating at least a portion of the first portion of the target tissue with the ultrasound transducer using the tissue-ablation map so as to form a conduction block that blocks aberrant electrical pathways in the heart.

2. The method of claim 1, wherein the advancing comprises transseptally crossing an atrial septum of the heart with the ultrasound transducer.

3. The method of claim 1, wherein the tissue-ablation map indicates current gap distances and previous gap distances associated with the target tissue.

4. The method of claim 1, wherein the identifying the first portion of the target tissue as ablation tissue is based at least in part on gap distance data indicated by the reflected ultrasound energy.

5. The method of claim 1, wherein the identifying the first portion of the target tissue as ablation tissue is based at least in part on data generated from the reflected ultrasound energy indicating one or more of tissue thickness, tissue type, identification of collateral tissue, lesion depth, presence of electrical signals, and tissue motion, as indicated by the reflected ultrasound energy.

6. The method of claim 1, further comprising:

generating gap distance data associated with the target tissue based on the reflected ultrasound energy; and identifying a pulmonary vein ostium based on the gap distance data;

wherein said second portion of the target tissue comprises identifying the pulmonary vein ostium as non-ablation tissue.

7. The method of claim 1, wherein:

the identifying the first portion of the target tissue as ablation tissue comprises determining that the first portion of the target tissue is associated with a first portion of the reflected ultrasound energy indicating tissue characteristic values that fall into a pre-defined range of values; and the identifying the second portion of the target tissue as non-ablation tissue comprises determining that the second portion of the target tissue is associated with a second portion of the reflected ultrasound data indicating tissue characteristic values that fall outside of the pre defined range of values.

8. The method of claim 7, further comprising identifying a third portion of the target tissue as borderline ablation tissue based at least in part on the reflected ultrasound energy.

9. The method of claim 1, wherein the tissue-ablation map visually indicates motion of the target tissue as the heart expands and contracts.

10. The method of claim 1, further comprising anchoring a wire in a pulmonary vein of the heart, wherein the ultrasound transducer is anchored by the wire during said emitting the ultrasound energy and receiving the reflected ultrasound energy.

11. The method of claim 1, further comprising identifying anatomical structures based on the reflected ultrasound energy.

12. The method of claim 1, further comprising identifying a center point of source of atrial fibrillation based on the reflected ultrasound energy.

13. The method of claim 1, further comprising generating an ablation path through the target tissue based at least in part on the reflected ultrasound energy.

14. The method of claim 13, further comprising determining that the ablation path meets tissue characteristic conditions based at least in part on tissue characteristic values associated with the reflected ultrasound energy.

15. The method of claim 13, wherein the tissue-ablation path represents:

the tissue-ablation path; and one or more excluded zones of the tissue-ablation path.

* * * * *